(12) United States Patent
Phopase et al.

(10) Patent No.: US 11,896,705 B2
(45) Date of Patent: Feb. 13, 2024

(54) FUNCTIONALIZED POLYPEPTIDES USEFUL IN HAIR TREATMENT

(71) Applicants: Ferentis, UAB, Vilnius (LT); Ranjithkumar Ravichandran, Linkoping (SE)

(72) Inventors: Jaywant Phopase, Linkoping (SE); Ranjithkumar Ravichandran, Linkoping (SE)

(73) Assignees: Uab FERENTIS, Vilnius (LT); Ranjithkumar Ravichandran, Linkoping (SE)

( * ) Notice: Subject to any disclaimer, the term of this patent is extended or adjusted under 35 U.S.C. 154(b) by 204 days.

(21) Appl. No.: 16/642,388

(22) PCT Filed: Aug. 24, 2018

(86) PCT No.: PCT/SE2018/000020
§ 371 (c)(1),
(2) Date: Feb. 27, 2020

(87) PCT Pub. No.: WO2019/045612
PCT Pub. Date: Mar. 7, 2019

(65) Prior Publication Data
US 2020/0188270 A1 Jun. 18, 2020

(30) Foreign Application Priority Data
Aug. 30, 2017 (SE) .................................. 1751041-3

(51) Int. Cl.
*A61K 8/65* (2006.01)
*A61Q 5/00* (2006.01)
*A61K 8/64* (2006.01)

(52) U.S. Cl.
CPC .................. *A61K 8/65* (2013.01); *A61K 8/64* (2013.01); *A61Q 5/002* (2013.01); *A61K 2800/82* (2013.01)

(58) Field of Classification Search
None
See application file for complete search history.

(56) References Cited

U.S. PATENT DOCUMENTS

| 2005/0176643 A1 | 8/2005 | Bridon et al. |
| 2011/0229568 A1 | 9/2011 | Oertel |
| | | (Continued) |

FOREIGN PATENT DOCUMENTS

| GB | 2541137 A | 2/2017 | |
| WO | WO-0045777 A1 * | 8/2000 | ............. A45D 20/38 |
| | | (Continued) | |

OTHER PUBLICATIONS

English translation of WO-0045777-A1 (Year: 2000).*

(Continued)

*Primary Examiner* — Nicole P Babson
(74) *Attorney, Agent, or Firm* — NIXON & VANDERHYE

(57) ABSTRACT

Disclosed is a polypeptide having a base amino acid sequence and wherein at least two amino acid residue side chains are substituted with functional Michael acceptor groups. Also disclosed are cosmetic compositions including the polypeptide, a method for repairing damaged hair using the polypeptide or composition, and to the use of the polypeptide or composition in such methods.

15 Claims, 2 Drawing Sheets
Specification includes a Sequence Listing.

(56) References Cited

U.S. PATENT DOCUMENTS

2014/0187651 A1* 7/2014 Hartgerink .............. A61L 27/52
530/356
2015/0034119 A1 2/2015 Pressly et al.
2015/0037270 A1 2/2015 Pressly et al.

FOREIGN PATENT DOCUMENTS

WO WO-2016044582 A1 * 3/2016 .............. A61K 8/19
WO WO2016/172708 10/2016
WO 2019/207447 A1 10/2019

OTHER PUBLICATIONS

International Search Report—PCT/SE2018/000020—dated Nov. 22, 2018.
Communication to applicant regarding observations by third parties from European Patent Office for European Serial No. EP18851777 (EP3703652), dated Jun. 4, 2021.
Supplementary European Search Report from European Patent Office for European Serial No. EP18851777 (EP3703652), dated Nov. 19, 2021.

\* cited by examiner

A                              B

FUNCTIONALIZED POLYPEPTIDES USEFUL IN HAIR TREATMENT

INCORPORATION BY REFERENCE

The text file named "polypeptide_ST25", created on Jul. 21, 2022, and sized 2153 bytes, which contains sequence ID listings, is herein expressly incorporated by reference.

TECHNICAL FIELD

The present invention relates to the field of cosmetics, and more specifically to agents, compositions and methods useful in treatment and repair as well as protection of hair.

BACKGROUND ART

Morphologically, hair fibers have three components called cuticle, cortex and medulla. Hair cortex is made of a cysteine rich protein (keratin) being linked through several disulphide bonds and covered by a thick layer of cuticle. The medulla is an inner core of the hair fiber. When the hair fiber is subjected to and damaged by either physical or chemical treatment (e.g. dying, bleaching, exposure to heat, light etc.), the damage causes changes in the physical properties of the hair fiber. Such damage includes premature fracture, longitudinal fibrillation, separation of hair cortex, loss of strength, loss of gloss and/or increased absorption. These damages ultimately lead to cleaving of the hair's cysteine disulphide bonds, leading to exposure of free thiols on the hair fiber.

Temporary solutions are available to treat the damaged hair with silicones or other hair conditioners, but as a result these treatments may create more damage to the hair. Other treatments such as Reduction methods (Thioglycolic acid or Ammonium Salt) and Oxidation methods (Sodium Bromate, hydrogen peroxides) have been routinely used, but these treatments do not aid in permanent repair of the hair fiber, as the products acting on the hair are eventually washed off when washing and shampooing the hair.

In 2013, a product was introduced on the market under the name "Olaplex", comprising a synthetic molecule, bis-aminopropyl diglycol dimaleate (CAS No. 1629579-82-3), that aids in permanent hair repair. Also US2015/0037270 discloses compounds that may be used in permanent hair repair.

SUMMARY OF THE INVENTION

The object of the present invention is to provide a compound that may be used to treat and repair hair fibres. The object is further to provide a compound for hair repair that protects the hair from further damage. The object is attained by providing a functionalized polypeptide.

Thus, according to a first aspect, the present invention relates to a polypeptide comprising a base amino acid sequence and wherein at least two amino acid residue side chains are substituted with functional Michael acceptor groups.

According to a second aspect, the present invention relates to a cosmetic composition comprising the polypeptide above.

According to a third aspect, the present invention relates to a method of treatment of damaged hair fibres, using the polypeptide above.

According to a fourth aspect the present invention relates to the use of the polypeptide above in a method of treatment of damaged hair fibres.

DEFINITIONS

Figure 1:
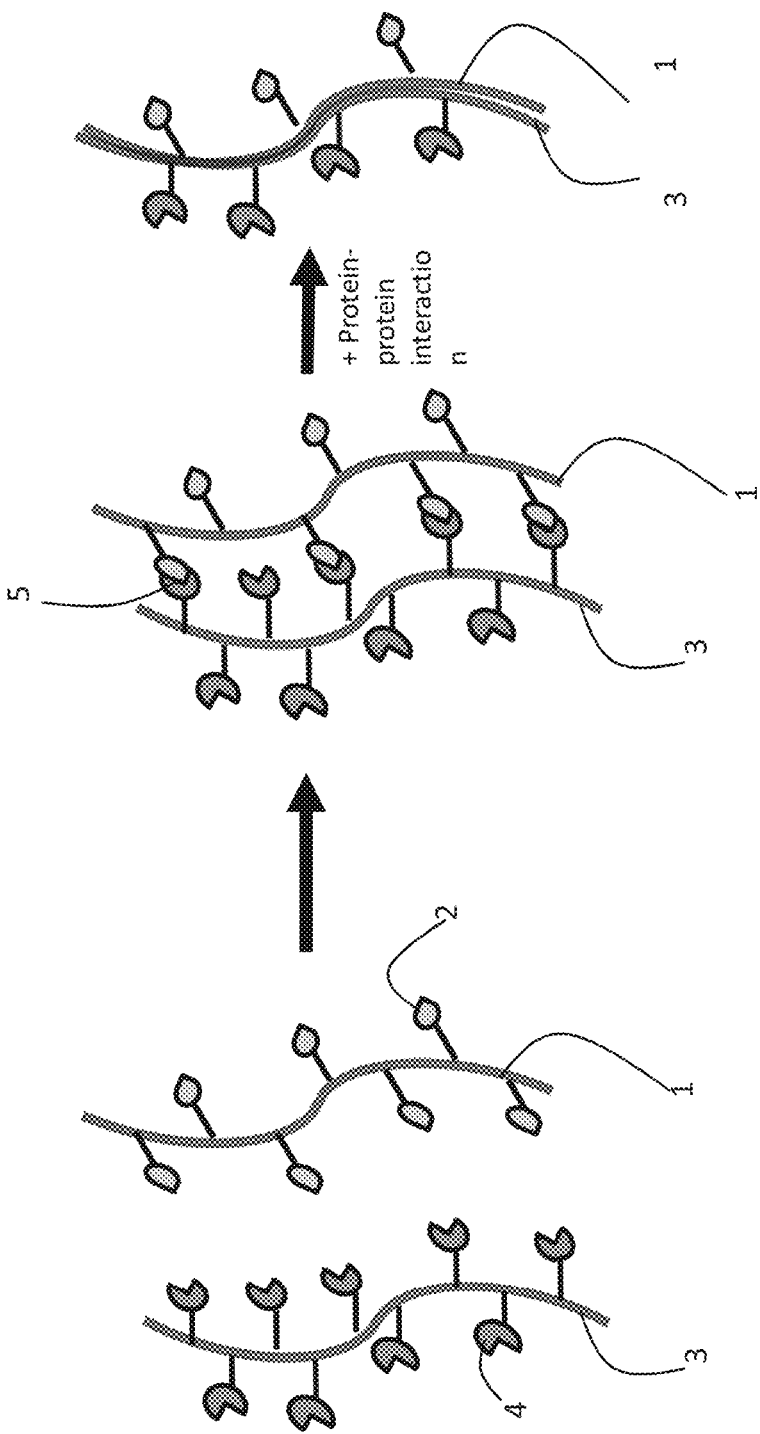
FIG. 1: Schematic of binding of the polypeptide according to the invention to the hair fibre.

With Michael addition, or Michael reaction, is meant a nucleophilic addition of a carbanion or another nucleophile, to an α,β-unsaturated carbonyl compound, or a C=C bond. It belongs to the larger class of conjugate additions, and is one of the most useful methods for the mild formation of C—C bonds. In Michael addition there is a Michael donor and a Michael acceptor, wherein the Michael donor has a slightly negative charge and can thus donate electrons. A Michael acceptor has a slightly positive charge and may accept electrons.

With thiol group, is meant an organosulfur compound R—S—H where R represents an alkyl or other organic substituent. Within the scope of the present invention, the thiol groups discussed are those present on cysteine residues within keratin. Normally, the thiol groups on the cysteines in keratin are bonded by disulphide bridges. Upon damage to the keratin, the disulphide bridges will break and the thiol groups will be free towards the environment as a negatively charged group.

With damaged hair is meant hair fibres having broken disulphide bridges, which results in free thiol groups on the hair fibre.

With Michael thiol click chemistry, or Thiol-ene reactions, is meant a reaction wherein thiols are conjugated to electron deficient C=C bonds, forming a thio-ester bond. Thereby the thiols will act as Michael donors, and the electron deficient C=C bonds will act as a Michael acceptor. Michael thiol reaction, or Thiol-ene reactions can be initiated by a wide variety of catalysts, light, heat or free radical initiators.

With thiol reactive group, or functional Michael acceptor group, is meant any chemical substance that comprises a C=C bond and can act as a Michael acceptor.

With maleimido, the group

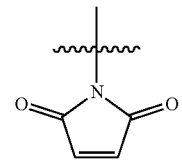 [SMILES: *N1C(=O)C=CC1=O]

is intended, wherein ⌇ indicates the bond through which the group is attached.

With acrylic, the group —C(=O)CH=CH$_2$ is intended. For instance, acrylic anhydride is the compound of the formula CH$_2$=CHC(=O)OC(=O)CH=CH$_2$.

With methacrylic, the group —C(=O)C(CH$_3$)=CH$_2$ is intended. For instance, methacrylic anhydride is the compound of the formula CH$_2$=C(CH$_3$)C(=O)OC(=O)C(CH$_3$)=CH$_2$.

With vinylsulfone, the group —S(=O)$_2$CH=CH$_2$ is intended.

"—" in front of the definition of a group indicates the group's point of attachment.

With base amino acid sequence is meant any base amino acid sequence that may be provided with at least two thiol-reactive groups or Michael acceptor groups. With Extracellular Matrix (ECM) protein is meant any protein that may naturally be present in the extracellular matrix that provides structural and biochemical support to surrounding cells.

Collagen is a structural protein in the extracellular space in various connective tissues in animal bodies, and the main component of skin and connective tissue, and it is the main organic component in bone and teeth. Fibrillar collagens belong to a family of structurally related collagens that form the characteristic collagen fibril bundles seen in connective tissue. Fibrillar collagen includes collagen type I, II, III, V, and XI. Non-fibrillar collagens are a family of structurally-related short-chain collagens that do not form large fibril bundles and include collagen type IV, VI, VI, IX, X, XII, XIII, XVIII, and endostatins.

With non-covalent protein-protein interaction is meant hydrogen bonds, ionic interactions, Van der Waals forces, or hydrophobic bonds between proteins. A hydrogen bond is the electrostatic attraction between two polar groups that occurs when a hydrogen (H) atom covalently bound to a highly electronegative atom such as nitrogen (N), oxygen (O), or fluorine (F) experiences the electrostatic field of another highly electronegative atom nearby. Van der Waals forces are distance dependent interactions between atoms. Unlike ionic or covalent bonds, these attractions are not a result of any chemical electronic bond and so this force is more susceptible to being perturbed and are relatively weak compared to covalent bonds. Ionic bonding is a type of chemical bond that involves the electrostatic attraction between oppositely charged ions, and hydrophobic bonding is an observed tendency of nonpolar substances to aggregate in aqueous solution and exclude water molecules.

DETAILED DESCRIPTION

The present invention aims to provide compounds useful in hair care products for repairing damaged hair fibres, as well as methods for repairing damaged hair and cosmetic compositions for use in such methods. Additionally, the present invention aims to provide such a compound that will protect the hair fibre from further damage.

There are products on the market, such as bis-aminopropyl diglycol dimaleate, which are used to repair damaged hair. However, treatment with bis-aminopropyl diglycol dimalate must be repeated at least once a week for a long-lasting effect on the hair. This is due to the fact that bis-aminopropyl diglycol dimalate is composed of cross-linking agents that are coupled to a backbone polymer via electrostatic bonds. Hence, upon every-day treatments of the hair, the electrostatic bonds will break and thus the closing of the disulphide bridge, accomplished by the product, will also break. Thus, there is a need for a more stable compound that may be used to repair and protect damaged hair.

Thus, in a first aspect the invention relates to a polypeptide having a base amino acid sequence and wherein at least two amino acid residue side chains are substituted with functional Michael acceptor groups. Preferably, the at least two amino acid residue side chains substituted with functional Michael acceptor groups are located on the surface of the polypeptide molecule so that said functional Michael acceptor groups are accessible for free thiol groups on other polypeptides, such as those on damaged hair fibres.

The base amino acid sequence of the polypeptide according to the invention may be the sequence of a natural protein, such as a protein being a normal constituent of the extracellular matrix (ECM) or a synthetic peptide. By using a polypeptide, a large molecule for treatment of damaged hair is obtained, and said polypeptide will cover a larger portion of the damaged hair, as compared to the prior art mentioned above. A large molecule also makes it possible to conjugate a large number of functional Michael acceptor groups to said molecule.

The functional Michael acceptor groups are covalently conjugated to any amino acid residues that comprise an amino group or a carboxyl group on a side chain of the base amino acid sequence. The amino acid residue may be any natural or unnatural amino acid that has an amino or carboxyl side chain group.

In one embodiment, the amino acid residue comprise an amino group and the substituted amino acid residue will have the formula

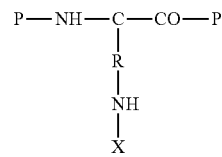

wherein P is the polypeptide, R is an amino acid side chain, and X is the functional Michael acceptor group. In the case where the Michael acceptor group is bound to a lysine residue, R is CH$_2$—CH$_2$—CH$_2$—CH$_2$.

The number of functional Michael acceptor groups, conjugated to the polypeptide, is determined by different factors. The length of the base amino acid sequence is a first factor that will decide the number of functional Michael acceptor groups conjugated to the polypeptide. A second factor is the amount of amino acid residues having an amino and/or carboxylic acid side chain group within the base amino acid sequence. According to the present invention, at least two amino acid residue side chains are substituted with functional Michael acceptor groups. Consequently, according to the present invention, the base amino acid sequence will comprise at least two amino acid residues having side chain groups which can be substituted with Michael acceptor functional groups, such as amino or carboxyl side chain groups.

Preferably, the amino acid residues to which the functional Michael acceptor groups are conjugated are lysines. Lysines have an amino side chain that can easily be derivatized into a Michael acceptor group. Thus, the base amino acid sequence may preferably comprise at least two lysine residues. However, any unnatural amino acid comprising an amino group or a carboxyl group may also be used within the base amino acid sequence.

The base amino acid sequence comprised in the polypeptide according to the invention is functionalized with functional Michael acceptor groups that may react with thiol groups as Michael donors. The functional Michael acceptor groups may be any Michael acceptors that may be coupled to the base amino acid sequence. The functional Michael acceptor groups are preferably chosen from the group comprising acrylic, methacrylic, maleimido or vinyl sulfone groups. These Michael acceptor groups are easily conjugated to an amino side chain on the base amino acid sequence. Furthermore, they are easily conjugated to any lysine residue within the base amino acid sequence.

The number of amino acids in the base amino acid sequence is preferably from about 25 to about 1000 amino acids.

The base amino acid sequence may be the sequence of any polypeptide. Preferably, the polypeptide is hydrophilic. Preferably, the base amino acid sequence is the sequence of an Extracellular matrix (ECM) protein, a fragment thereof, or ECM protein mimetic peptide. The ECM protein may further be chosen from the group comprising of collagen type I, II, III and IV, gelatin, and keratin. By mimetic is meant that the peptide can structurally mimic the protein being mimicked. When the base amino acid sequence is the sequence of an ECM protein mimetic peptide, it is preferably the sequence of a collagen mimetic peptide. In this particular case, it means that the collagen mimetic peptide can self-assemble into a triple-helix, and thus can mimic the triple helical assembly of collagen.

The collagen mimetic peptide may preferably have the following amino acid sequence:

```
                                              (SEQ ID NO: 1)
Gly-(Pro-Lys-Gly)4(Pro-Hyp-Gly)4(Asp-Hyp-Gly)4,
or
                                              (SEQ ID NO: 2)
(Pro-Lys-Gly)4(Pro-Hyp-Gly)4(Asp-Hyp-Gly)4.
```

When the collagen mimetic peptide above is used as the base amino acid sequence in the polypeptide according to the invention, 2, 3 or 4 side chains of amino acid residues are substituted with functional Michael acceptor groups. Preferably 2 or 4 residues are substituted, and more preferably 4 residues are substituted.

According to one embodiment of the invention, where porcine collagen is used as the base amino acid sequence, the maximum number of modified lysine residues substituted with functional Michael acceptor groups is 114 lysine residues. Thus, according to the present invention, the base amino acid sequence may comprise 2-114 amino acid residues that are substituted with functional Michael acceptor groups.

Interaction of the polypeptide according to the invention with the hair fibre, in particular binding to free thiols on said hair fibre, is obtained via a Michael thiol click chemistry reaction. The free thiols on the hair fibre act as Michael donors in said reaction. At each single breaking point of the cysteine disulphide bonds on the hair fiber, there will be two free thiol groups exposed as a result of the broken disulphide bonds. Thus there must be at least two functional Michael acceptor groups available on the polypeptide according to the invention, in order to be able to bind to both of the two free thiol groups, thus closing the gap and the point of damage on the hair. Thus, also there should preferably always be an even number of functional Michael acceptor groups on the polypeptide. According to the present invention, 2-114 functional Michael acceptor groups may be present on the polypeptide.

In addition to the Thiol-Michael addition reaction between the free thiol groups on the hair fibre and the Michael acceptor groups on the polypeptide according to the invention, there are also interactions between the base amino acid sequence and lipids, such as 18-methyl eicosanoic acid, or hair proteins on the hair fibre. These interactions are accomplished by protein-protein interaction, such as electrostatic, ionic, hydrophobic or Van der Waals reactions as well as hydrogen bonds.

This non-covalent bonding further strengthens the bonding between the polypeptide according to the invention and the hair fibre. The protein-protein interactions may occur both on areas where the hair is damaged, and on non-damaged areas of the same hair fibre. Thus, treatment of damaged hair is obtained by covalent binding of the free thiol groups on the hair fibre to the polypeptide of the invention, as well as non-covalent protein-protein interactions between the polypeptide according to the invention and the hair fibre.

FIG. 1 is a schematic drawing illustrating the polypeptide (1) of the invention having functional Michael acceptors (2) and the hair fibre (3) with free thiol groups (4) present. As illustrated in FIG. 1, the functional Michael acceptors (2) on the polypeptide (1) according to the invention will, together with the free thiol groups (4) which are present on the hair fibre (3) as a result broken disulphide bridges, cause a covalent bond (5) between the hair fibre (3) and the polypeptide (1). Furthermore, protein-protein interactions will occur between the proteins present in the hair fibre, and the polypeptide according to the invention, further strengthening the binding between the polypeptide (1) and the hair fibre (3).

Additionally, because of the length of the base amino acid sequence and consequently the length of the polypeptide, said polypeptides of the invention will more easily cover a large part of the hair fibre, and may ultimately form a protecting layer surrounding the entire hair fibre. Such a protecting layer is covalently bound to the hair fibre by said Michael thiol click chemistry reaction, as well as bound to the hair fibre by the other interactions specified above. Thus, apart from repair of damaged areas such as broken disulphide bonds on the hair fibre, the entire hair fibre will be protected, by means of the protecting layer formed, against further damage to the hair fibre, such as by various hair treatments. For instance, the hair fibre will be protected by the protective layer from damage that may otherwise be caused by heat treatments such as blow drying or using other heat appliances for hair styling.

Figure 2:
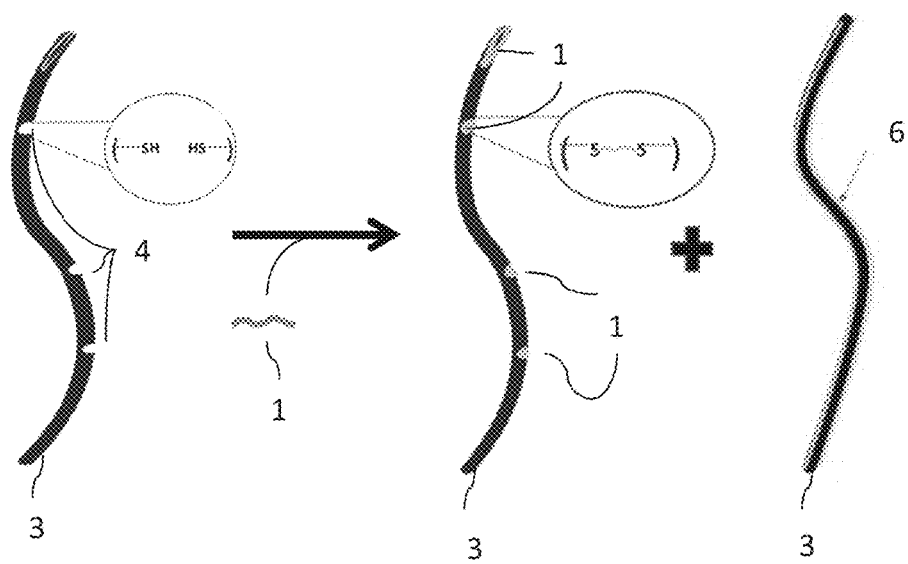
FIG. 2: Schematic of binding of the polypeptide according to the invention to hair fibre, illustrating repair of damage on the hair fibre and formation of a protective layer on the hair fibre.

FIG. 2 illustrates the repair of the broken disulphide bridges (4) on the hair fibre (3) by the polypeptide of the invention (1), as well as the binding of the polypeptide of the invention (1) to the rest of the hair fibre by protein-protein interactions. Consequently a protective layer (6) is formed over the entire hair fibre.

Figure 3:
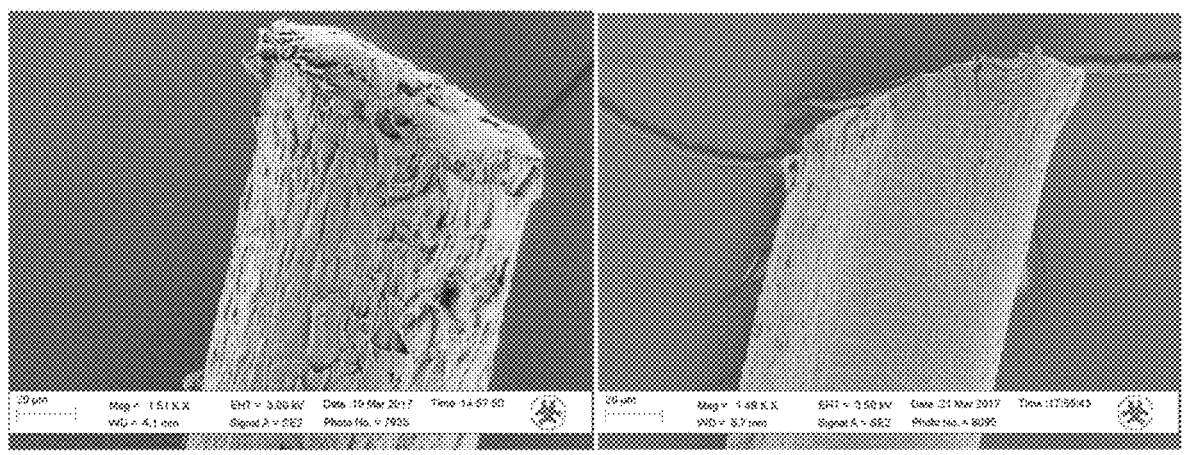
FIG. 3: Scanning Electron Microscopic (SEM) images showing the difference in morphology between a damaged hair fiber before (A) and after (b) treatment with the polypeptide according to the invention.

FIG. 3 shows Scanning Electron Microscopic (SEM) pictures of a hair fibre before (a) and after (b) treatment of the hair fibre with a functionalized polypeptide according to the invention (maleimide collagen type 1). Before the treatment (FIG. 3a), a jagged surface is seen, caused by broken disulphide bridges in the hair cortex. After treatment of the hair fibre with the polypeptide of the invention (FIG. 3b), the surface of the hair fibre is smooth due to a repair of the sulphur-sulphur bridging. A set of hair comprising the hair fibres according to the FIG. 3b will be glossy and shiny as well as smooth to the feeling.

Due to the covalent links to the hair fibre, accomplished by the Michael thiol click chemistry reactions, the polypeptide of the invention will additionally be more durable, resist wearing off and will not be easily washed off the hair upon washing and shampooing thereof. As a consequence, also the protecting layer formed, attached by both covalent links and protein-protein interactions, will be more durable and not easily washed off. Thus, treatment of the hair with the polypeptide of the invention can be performed less often with maintained effect, as compared to the prior art.

An additional effect of the polypeptide according to the present invention is that it will provide a moisturizing effect on the hair. The moisturizing effect is attained due to the fact that the proteins or peptides used as the base amino acid sequence are hydrophilic and thus will absorb water. This moisturizing property will contribute to a hair that is glossy, shiny and smooth.

According to a second aspect of the invention, a cosmetic composition may be provided comprising the polypeptide according to the invention. Such a cosmetic composition may additionally comprise any cosmetically acceptable excipients, and/or carriers.

In one embodiment, the cosmetic composition is an aqueous cosmetic composition.

In one embodiment, the aqueous cosmetic composition has a pH in the range 7.4-10, such as 7.4, 8, 8.5, 9, 9.5 or 10.

In one embodiment, the cosmetic composition comprises 1-5% of the polypeptide according to the invention, such as 1%, 2%, 3%, 4% or 5% of the polypeptide according to the invention.

In one embodiment, the cosmetic composition further comprises a photoinitiator. An exemplary photoinitiator is 2-Hydroxy-4'-(2-hydroxyethoxy)-2-methylpropiophenone (also known as Irgacure 2959).

According to a third aspect of the invention, a method for treatment and/or repair of damaged hair fibres is provided. The method of treatment comprises bringing the polypeptide of the invention, or the cosmetic composition according to the invention, into contact with damaged hair fibres. The polypeptide should remain in contact with the damaged hair for a time period sufficient for the Michael acceptor groups on the polypeptide to react with free thiol groups on the damaged hair fibres. The time period may be at least 15 minutes, such as at least 20 minutes, or at least 30 minutes. During this time, additional polypeptide or composition according to the invention may be added to and brought into contact with the damaged hair. Excess polypeptide is then washed away, using a suitable hair cleaning composition.

The treatment of hair fibres with the polypeptide or cosmetic composition according to the invention should be allowed to proceed for a time period of at least 15 minutes, preferably at least 20 minutes, and more preferably at least 30 minutes.

The treatment may be performed by a first application of the polypeptide or cosmetic composition to the hair fibres for a first time period, and thereafter a second application of the polypeptide or the cosmetic composition for a second time period, without rinsing the hair fibres with water in between the applications. After the second time period, the hair fibres are rinsed with water and optionally washed with a shampoo and optionally a conditioner. After both the first and second application of the polypeptide or cosmetic composition according to the invention to the hair fibres, the treatment may have a duration according to any the specified time periods above. The total time period of treatment for a double application should be at least 30 minutes, preferably at least 35 minutes. It may be advantageous to allow a longer time period after the second application compared to after the first application.

Treatment of the hair with the polypeptide according to the invention may be performed once a month, or once every two months, or even less often. The inventors have observed that 2 months after treatment of hair with the polypeptide according to the invention, no changes to the hair morphology from what is shown in FIG. 3b was observed. This is due to the covalent attachment of the functional Michael acceptor groups to the base amino acid sequence, which is not easily broken by every day treatments of the hair fibre. Thus the polypeptide remains intact as well as covalently bound to the hair fibre. This is compared to the prior art where electrostatic attachments are used within the active ingredient, which are less stable, and consequently may more easily be broken, causing the disulphide bridges to break again.

In some embodiments, a photoinitiator is brought into contact with the damaged hair fibres in addition to the polypeptide according to the invention. The method then further comprises irradiating the damaged hair fibres with UV-light (e.g. 365 nm) for 30 seconds to 5 minutes.

The method for treatment of damaged and/or repair of damaged hair fibres may be a cosmetic method.

According to a fourth aspect of the invention, the use of a polypeptide and/or the cosmetic composition according to the present invention is provided in a method for repairing damaged hair fibres.

EXAMPLES

1. Materials

Freeze dried porcine collagen was purchased from NIPPON meat packers, Japan, collagen mimetic peptide [Gly-(Pro-Lys-Gly)$_4$(Pro-Hyp-Gly)$_4$(Asp-Hyp-Gly)$_4$] and (Pro-Lys-Gly)$_4$(Pro-Hyp-Gly)$_4$(Asp-Hyp-Gly)$_4$ were synthesized on a Symphony automated peptide synthesizer (Protein Technologies Inc., Tucson, AZ, U.S.A.). Type A gelatin from porcine skin (gel strength 300 bloom), Sodium hydroxide, methacrylic anhydride, 2-Hydroxy-4'-(2-hydroxyethoxy)-2-methylpropiophenone, Dithiothreitol (DTT) and 60% solution of Ammonium thioglycolate (ATG) were purchased from Sigma-Aldrich, St. Louis, USA. Acrylic anhydride was purchased from abcr GmbH Germany 3-(Maleimido)propionic acid N-hydroxysuccinimide ester and 6-Maleimidohexanoic acid N-hydroxysuccinimide were purchased from Chem-Impex International, Inc. Human hairs were obtained and subjected to disulfide damage by treatment with DTT (3 wt % in water) or ATG (5 wt % in water) for 15 minutes, 30 minutes and 1 hr. The hairs were then rinsed for 2 minutes with water, and then dried with a towel.

2. Functionalization of Collagen, Collagen Mimetic Peptide (CMP) and Gelatin 2.1 Synthesis of Methacrylated Collagen/Collagen Mimetic Peptide/Gelatin and Acrylated Collagen Freeze dried collagen/CMP/gelatin was dissolved in Milli Q water and gently stirred. The pH of the solution was increased to pH 10 using 2N NaOH and acrylic anhydride/methacrylic anhydride at a molar ratio of 5:1 (with respect to number of lysine amine groups in collagen/CMP) was added subsequently drop-wise at room temperature and stirred for 3 hours. The reaction mixture was dialyzed against distilled water using 12-14 kDa cutoff dialysis tubing (Spectrum Laboratories, Inc., CA, US) for 2 days to remove reaction by-products and freeze dried and stored at 4° C. until further use.

2.2 Synthesis of Maleimide Collagen/Collagen Mimetic Peptide (CMP)/Gelatin

Freeze dried collagen/CMP/gelatin was dissolved in Milli Q water and the pH of the solution was adjusted to pH 10 using 2N NaOH. The solution of 6-Maleimidohexanoic acid N-hydroxysuccinimide in DMSO (3:1 molar ratio with respect to number of lysine amine groups in collagen/CMP) was added drop-wise at room temperature and stirred for 3 hours. The reaction mixture was dialyzed against distilled water using 12-14 kDa cutoff dialysis tubing (Spectrum Laboratories, Inc., CA, US) for 2 days to remove reaction by-products and freeze dried and stored at 4° C. until further use.

2.3 Characterization of Functionalized Collagen, Collagen Mimetic Peptide (CMP), Gelatin Tri-Nitro Benzene Sulfonic Acid (TNBS) Assay The extent of modification of collagen, gelatin and CMP was quantified using TNBS (2,4,6-trinitrobenzenesulfonic acid) calorimetric assay. Briefly, 2 mg of dry sample was mixed with 1 ml of 4 wt % NaHCO3 (pH 8.5) and 1 ml of 0.5 wt % TNBS solution at 40° C. under mild shaking. After 4 hours of reaction, 3 mL of 6M HCl solution was added and the mixture was heated to 90° C. to dissolve any sample residuals. Then the solutions were cooled and extracted three times with anhydrous diethyl ether to remove the unreacted TNBS species. UV absorbance of samples was recorded using Shimadzu UV-Vis spectrophotometer (UV-2450) against a blank, prepared by the above procedure, except that the HCl solution was added before the addition of TNBS. The content of free amino acid groups and degree of functionalization (F) were calculated as follows:

$$\frac{\text{moles (Lys)}}{g(\text{collagen})} = \frac{2 \cdot \text{Abs}_{346} \cdot 0.02}{1.46 \cdot 10^4 \cdot b \cdot x} \quad (1)$$

$$F = 1 - \frac{\text{moles (Lys) modified collagen}}{\text{moles (Lys) pristine collagen}} \quad (2)$$

where Abs $(_{346})$ is the absorbance value at 346 nm, $1.4 \times 10^4$ is the molar absorption coefficient for 2, 4, 6-trinitrophenyl lysine (I. mol$^{-1}$·cm$^{-1}$), b is the cell path length (1 cm), x is the sample weight and moles (Lys) modified collagen and moles (Lys) pristine collagen represent the lysine molar content in functionalized and pristine collagen, respectively.

Nuclear Magnetic Resonance

Structural properties of functionalized collagen/CMP/gelatin were analyzed by $^1$H NMR spectroscopy, using a 500 MHz Varian Inova NMR spectrometer equipped with a cryoprobe (data not shown).

3. General Method for Hair Crosslinking Method

Functionalized polypeptide solution in Milli Q water (0.1-10% w/w) was applied on the damaged hairs thoroughly using brush. The hairs were laid on aluminum foil and allowed to process for 15 minutes. The crosslinking solution was applied second time on the hairs and left for 20 minutes. The hairs were then washed with shampoo and rinsed thoroughly with water and air dried. The washing and drying step was repeated for 10 times.

3.1 Maleimide Functionalized Polypeptide

Crosslinking formulation used: Maleimide collagen (1% in water).

Method:

Human hairs were obtained and cut in 1 cm wefts. Four hair samples were washed with shampoo and dried with towel. DTT (3% in water) was applied on one sample while ATG (5 wt % in water) was applied on second sample and left for 15 minutes to 1 hour. The hairs were then washed thoroughly with water and dried with towel.

The crosslinking formulation was then applied to the hairs thoroughly using brush or spray, soaking the hairs. The crosslinking solution was left to process for (2-15 minutes). The crosslinking solution was applied second time on the hairs and left for 10-20 minutes. The hairs were then washed with shampoo and rinsed thoroughly with water and air dried. The washing and drying step was repeated for 10 times.

Another two hair samples, one treated with DTT and second sample treated with ATG as above, except the crosslinking solution was not applied were used as control for comparison study.

Result: The hair samples treated with crosslinking formulation showed no sign of breakage and showed similar strength and appearance compared to the untreated virgin hair. The hair samples treated with crosslinking formulation showed higher thickness and strength and showed more shine and healthier appearance compared to the control samples.

This method can be applied also using Maleimide collagen mimetic peptide (3% in water) or Maleimide gelatin (1-3% in water).

3.2 Methacrylated Polypeptides

Crosslinking formulation: Methacrylated gelatin (3% in water, pH=8-9)

Method:

Human hairs were obtained and cut in 1 cm wefts. Two hair samples were washed with shampoo and dried with towel. DTT (3% in water) was applied on one sample while ATG (5 wt % in water) was applied on second sample and left for 15 minutes to 1 hour. The hairs were then washed thoroughly with water and dried with towel.

The crosslinking formulation was then applied to the hairs thoroughly using brush or spray, soaking the hairs. The crosslinking solution was left to process for (2-15 minutes). The crosslinking solution was applied second time on the hairs and left for 10-20 minutes. The hairs were then washed with shampoo and rinsed thoroughly with water and air dried. The washing and drying step was repeated for 10 times.

Another two hair samples, one treated with DTT and second sample treated with ATG as above, except the crosslinking solution was not applied were used as control for comparison study.

Result: The hair samples treated with crosslinking formulation showed no sign of breakage and showed similar strength and appearance compared to the untreated virgin hair. The hair samples treated with crosslinking formulation showed higher thickness and strength and showed more shine and healthier appearance compared to the control samples.

This method can be applied also using Methacrylated collagen (1% in water, pH=8-9) or Methacrylated collagen mimetic peptide (3% in water, pH=8-9).

3.3 Methacrylated Gelatin in Combination with a Photoinitiator and UV Light

Crosslinking formulation: Methacrylated gelatin (3%)+ (0.2%) 2-Hydroxy-4'-(2-hydroxyethoxy)-2-methylpropiophenone (Irgacure 2959) in water.

Method:

Human hairs were obtained and cut in 1 cm wefts. Two hair samples were washed with shampoo and dried with towel. DTT (3% in water) was applied on one sample while ATG (5 wt % in water) was applied on second sample and left for 15 minutes to 1 hour. The hairs were then washed thoroughly with water and dried with towel.

The crosslinking formulation was then applied to the hairs thoroughly using brush or spray, soaking the hairs. The soaked hair sample was exposed to UV light (365 nm) for 30 sec to 5 minutes. The crosslinking solution was further left to process for (1-10 minutes). The hairs were then washed with shampoo and rinsed thoroughly with water and air dried. The washing and drying step was repeated for 10 times.

Another two hair samples, one treated with DTT and second sample treated with ATG as above, except the crosslinking solution was not applied were used as control for comparison study.

Result: The hair samples treated with crosslinking formulation showed no sign of breakage and showed higher thickness and more shine and healthier appearance compared to the control samples.

This method can be applied also using Methacrylated collagen (1% in water) or Methacrylated collagen mimetic peptide (3% in water).

5. Analysis of Hair Strength

The strength of hairs after treatment with a functionalized polypeptide according to the invention was compared to untreated and damaged hair (treated with ATG/DTT). The comparison was performed by fixing the hair at one end and attaching a weight on the other end. The treated hair can hold approximately 40 g more weight compared to the damaged hair (treated with ATG/DTT).

The invention claimed is:

1. A cosmetic composition comprising a polypeptide for hair repair comprising:
   a polypeptide base amino acid sequence (P), and
   at least two amino acid residue side chains from the polypeptide base amino acid sequence (P),
   wherein the at least two amino acid residue side chains are substituted with functional Michael acceptor groups,
   wherein at least one of the at least two amino acid residue side chains has the Michael acceptor group (X) conjugated to the amino base of the amino acid residue (R), conforming to the following structure:

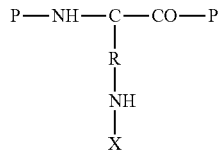

wherein the polypeptide base amino acid sequence (P) is from about 25 to about 1000 amino acids and is selected from the group consisting of: a natural protein or a fragment thereof and Gly-(Pro-Lys-Gly)$_4$(Pro-Hyp-Gly)$_4$(Asp-Hyp-Gly)$_4$ or (Pro-Lys-Gly)$_4$(Pro-Hyp-Gly)$_4$(Asp-Hyp-Gly)$_4$.

2. The cosmetic composition according to claim 1, wherein at least one of the at least two amino acid residue side chains substituted with functional Michael acceptor groups comprises a carboxyl group.

3. The cosmetic composition according to claim 2, wherein the at least two amino acid residues having side chains substituted with functional Michael acceptor groups are lysine residues.

4. The cosmetic composition according to claim 2, wherein the polypeptide base amino acid sequence corresponds to an Extracellular matrix (ECM) protein or a fragment thereof.

5. The cosmetic composition according to claim 1, wherein the at least two amino acid residues having side chains substituted with functional Michael acceptor groups are lysine residues.

6. The cosmetic composition according to claim 2, wherein the polypeptide base amino acid sequence is Gly-(Pro-Lys-Gly)$_4$(Pro-Hyp-Gly)$_4$(Asp-Hyp-Gly)$_4$, or (Pro-Lys-Gly)$_4$(Pro-Hyp-Gly)$_4$(Asp-Hyp-Gly)$_4$, and wherein 2, 3, or 4 side chains of amino acid residues are substituted with functional Michael acceptor groups.

7. The cosmetic composition according to claim 5, wherein the polypeptide base amino acid sequence corresponds to an Extracellular matrix (ECM) protein or a fragment thereof.

8. The cosmetic composition according to claim 1, wherein the polypeptide base amino acid sequence corresponds to an Extracellular matrix (ECM) protein or a fragment thereof.

9. The cosmetic composition according to claim 8, wherein the ECM protein is gelatin, keratin or collagen Type I, II, III or IV, or a fragment thereof.

10. The cosmetic composition according to claim 1, wherein the polypeptide base amino acid sequence is Gly-(Pro-Lys-Gly)$_4$(Pro-Hyp-Gly)$_4$(Asp-Hyp-Gly)$_4$ or (Pro-Lys-Gly)$_4$(Pro-Hyp-Gly)$_4$(Asp-Hyp-Gly)$_4$, and wherein 2, 3, or 4 side chains of amino acid residues are substituted with functional Michael acceptor groups.

11. The cosmetic composition according to claim 1, being an aqueous composition with a pH in the range 7.4-10.

12. The cosmetic composition according to claim 1, comprising 1%-5% of the polypeptide.

13. The cosmetic composition according to claim 1, further comprising a photoinitiator.

14. Method for repair of damaged hair fibres, comprising bringing the cosmetic composition according to claim 13 in contact with the damaged hair fibres.

15. Method according to claim 14, said method further comprising irradiating the damaged hair fibres with UV-light.

* * * * *

SEQUENCE LISTING

```
<160> NUMBER OF SEQ ID NOS: 2

<210> SEQ ID NO 1
<211> LENGTH: 37
<212> TYPE: PRT
<213> ORGANISM: Sus scrofa
<220> FEATURE:
<221> NAME/KEY: MISC_FEATURE
<222> LOCATION: (15)..(15)
<223> OTHER INFORMATION: Hydroxyproline
<220> FEATURE:
<221> NAME/KEY: MISC_FEATURE
<222> LOCATION: (18)..(18)
<223> OTHER INFORMATION: Hydroxyproline
<220> FEATURE:
<221> NAME/KEY: MISC_FEATURE
<222> LOCATION: (21)..(21)
<223> OTHER INFORMATION: Hydroxyproline
<220> FEATURE:
<221> NAME/KEY: MISC_FEATURE
<222> LOCATION: (24)..(24)
<223> OTHER INFORMATION: Hydroxyproline
<220> FEATURE:
<221> NAME/KEY: MISC_FEATURE
<222> LOCATION: (27)..(27)
<223> OTHER INFORMATION: Hydroxyproline
<220> FEATURE:
<221> NAME/KEY: MISC_FEATURE
<222> LOCATION: (30)..(30)
<223> OTHER INFORMATION: Hydroxyproline
<220> FEATURE:
<221> NAME/KEY: MISC_FEATURE
<222> LOCATION: (33)..(33)
<223> OTHER INFORMATION: Hydroxyproline
<220> FEATURE:
<221> NAME/KEY: MISC_FEATURE
<222> LOCATION: (36)..(36)
<223> OTHER INFORMATION: Hydroxyproline

<400> SEQUENCE: 1

Gly Pro Lys Gly Pro Lys Gly Pro Lys Gly Pro Lys Gly Pro Xaa Gly
1               5                   10                  15

Pro Xaa Gly Pro Xaa Gly Pro Xaa Gly Asp Xaa Gly Asp Xaa Gly Asp
            20                  25                  30

Xaa Gly Asp Xaa Gly
        35

<210> SEQ ID NO 2
<211> LENGTH: 36
<212> TYPE: PRT
<213> ORGANISM: Sus scrofa
<220> FEATURE:
<221> NAME/KEY: MISC_FEATURE
<222> LOCATION: (14)..(14)
<223> OTHER INFORMATION: Hydroxyproline
<220> FEATURE:
<221> NAME/KEY: MISC_FEATURE
<222> LOCATION: (17)..(17)
<223> OTHER INFORMATION: Hydroxyproline
```

```
<220> FEATURE:
<221> NAME/KEY: MISC_FEATURE
<222> LOCATION: (20)..(20)
<223> OTHER INFORMATION: Hydroxyproline
<220> FEATURE:
<221> NAME/KEY: MISC_FEATURE
<222> LOCATION: (23)..(23)
<223> OTHER INFORMATION: Hydroxyproline
<220> FEATURE:
<221> NAME/KEY: MISC_FEATURE
<222> LOCATION: (26)..(26)
<223> OTHER INFORMATION: Hydroxyproline
<220> FEATURE:
<221> NAME/KEY: MISC_FEATURE
<222> LOCATION: (29)..(29)
<223> OTHER INFORMATION: Hydroxyproline
<220> FEATURE:
<221> NAME/KEY: MISC_FEATURE
<222> LOCATION: (32)..(32)
<223> OTHER INFORMATION: Hydroxyproline
<220> FEATURE:
<221> NAME/KEY: MISC_FEATURE
<222> LOCATION: (35)..(35)
<223> OTHER INFORMATION: Hydroxyproline

<400> SEQUENCE: 2

Pro Lys Gly Pro Lys Gly Pro Lys Gly Pro Lys Gly Pro Xaa Gly Pro
1               5                   10                  15

Xaa Gly Pro Xaa Gly Pro Xaa Gly Asp Xaa Gly Asp Xaa Gly Asp Xaa
            20                  25                  30

Gly Asp Xaa Gly
            35
```